(12) United States Patent
Jensen

(10) Patent No.: US 11,622,674 B2
(45) Date of Patent: Apr. 11, 2023

(54) ARTICULATED TIP PART FOR AN ENDOSCOPE

(71) Applicant: AMBU A/S, Ballerup (DK)

(72) Inventor: Thomas Bachgaard Jensen, Copenhagen V (DK)

(73) Assignee: AMBU A/S, Ballerup (DK)

( * ) Notice: Subject to any disclaimer, the term of this patent is extended or adjusted under 35 U.S.C. 154(b) by 511 days.

(21) Appl. No.: 16/599,488

(22) Filed: Oct. 11, 2019

(65) Prior Publication Data

US 2020/0113412 A1 Apr. 16, 2020

(30) Foreign Application Priority Data

Oct. 12, 2018 (EP) ..................................... 18199998

(51) Int. Cl.
*A61B 1/005* (2006.01)
*A61B 1/00* (2006.01)
(Continued)

(52) U.S. Cl.
CPC .......... *A61B 1/0055* (2013.01); *A61B 1/0051* (2013.01); *A61B 1/00097* (2022.02);
(Continued)

(58) Field of Classification Search
CPC ... A61B 1/0011; A61B 1/0051; A61B 1/0055; A61B 1/0056; A61B 1/0057;
(Continued)

(56) References Cited

U.S. PATENT DOCUMENTS

| 4,998,916 A | 3/1991 | Hammerslag et al. |
| 5,325,845 A * | 7/1994 | Adair ................... A61B 1/0055 600/114 |

(Continued)

FOREIGN PATENT DOCUMENTS

| JP | 2004008638 A | 1/2004 |
| JP | 2009279182 A | 12/2009 |

(Continued)

OTHER PUBLICATIONS

European Search Report in related EP Application No. 18199998, dated Apr. 5, 2019

(Continued)

*Primary Examiner* — Aaron B Fairchild
*Assistant Examiner* — Stephen Floyd London
(74) *Attorney, Agent, or Firm* — Faegre Drinker Biddle & Reath LLP

(57) ABSTRACT

An articulated tip part for an endoscope, and an endoscope, including segments including a distal end segment having an outer wall defining an inner spacing adapted to accommodate a camera assembly therein and a proximal wall having a proximal surface, the distal end segment having an outer surface, wherein adjacent of the segments are interconnected by at least one hinge member to enable bending of the articulated tip part; and an insertion guide adapted to guide a steering wire and including an entry provided in the outer surface of the distal end segment, the insertion guide also including an exit fluidly coupled with and leading to the inner spacing of the distal end segment, whereby an end of a steering wire can be guided into the inner spacing of the distal end segment via the entry of the insertion guide.

18 Claims, 11 Drawing Sheets

(51) Int. Cl.
*A61B 1/05* (2006.01)
*A61B 1/018* (2006.01)

(52) U.S. Cl.
CPC .......... *A61B 1/00114* (2013.01); *A61B 1/018* (2013.01); *A61B 1/05* (2013.01)

(58) Field of Classification Search
CPC . A61B 1/008; A61B 1/01; A61B 1/05; A61M 2025/015; A61M 25/007; A61M 25/0147
See application file for complete search history.

(56) References Cited

U.S. PATENT DOCUMENTS

| | | |
|---|---|---|
| 8,790,250 B2 | 7/2014 | Petersen et al. |
| 9,220,400 B2 | 12/2015 | Petersen |
| 10,321,804 B2 | 6/2019 | Jacobsen et al. |
| 11,471,031 B2 | 10/2022 | Jensen |
| 2002/0193663 A1 | 12/2002 | Matsuura |
| 2003/0040657 A1 | 2/2003 | Yamaya et al. |
| 2008/0242935 A1 | 10/2008 | Inoue |
| 2008/0266441 A1 | 10/2008 | Ichimura |
| 2009/0163917 A1* | 6/2009 | Potter ............... A61M 25/0147 606/41 |
| 2009/0227842 A1* | 9/2009 | Ando ................. A61B 1/0055 600/146 |
| 2009/0234192 A1 | 9/2009 | Okada |
| 2012/0095369 A1 | 4/2012 | Teixeira et al. |
| 2012/0296167 A1* | 11/2012 | Chen ................. A61B 1/00078 600/110 |
| 2013/0041223 A1* | 2/2013 | Kato .................... A61B 1/0051 600/121 |
| 2013/0041314 A1 | 2/2013 | Dillon |
| 2013/0090529 A1 | 4/2013 | Boulais |
| 2014/0187894 A1 | 7/2014 | Bui et al. |
| 2014/0210976 A1 | 7/2014 | Lin |
| 2014/0243592 A1* | 8/2014 | Kato ................. A61M 25/0147 600/104 |
| 2016/0051222 A1 | 2/2016 | Imahashi |
| 2017/0266410 A1* | 9/2017 | Farrell ................ A61B 5/6852 |
| 2018/0228346 A1 | 8/2018 | Sekowski et al. |
| 2018/0289242 A1 | 10/2018 | Dai |
| 2019/0167070 A1* | 6/2019 | Ide ........................ A61B 1/008 |
| 2019/0175007 A1 | 6/2019 | Sorensen et al. |
| 2019/0175875 A1* | 6/2019 | Mirzalou .......... A61M 25/0147 |
| 2019/0254504 A1 | 8/2019 | Ide |
| 2019/0388163 A1 | 12/2019 | Kim et al. |
| 2020/0016370 A1* | 1/2020 | Sasaki .................... A61M 1/84 |
| 2020/0046209 A1* | 2/2020 | Fancher .............. A61B 1/0011 |
| 2020/0100648 A1 | 4/2020 | Jensen |
| 2020/0187765 A1* | 6/2020 | Ide ........................ A61B 1/005 |
| 2021/0146096 A1 | 5/2021 | Yamada et al. |
| 2021/0219818 A1* | 7/2021 | Oyama ................ A61B 1/0051 |

FOREIGN PATENT DOCUMENTS

| | | |
|---|---|---|
| JP | 2010005277 A | 1/2010 |
| JP | 2011200399 A | 10/2011 |
| JP | 2015058118 A | 3/2015 |
| KR | 20160056725 A | 5/2016 |
| TW | 201825039 A | 7/2018 |
| WO | WO 2010/066790 A1 | 6/2010 |
| WO | WO 2014/106511 A1 | 7/2014 |
| WO | WO 2016/188543 A1 | 12/2016 |

OTHER PUBLICATIONS

European Extended Search Report in related EP Application No. 18199998, dated Apr. 18, 2019
Examination report in related European application No. 18 199 998.8 dated Oct. 19, 2022, 4 pgs.
Office Action received for Chinese Patent Application No. 201880025464, dated Jun. 27, 2022, 7 pages (4 pages of English Translation and 3 pages of Original Document).
Office Action received for Chinese Patent Application No. 201880025464, dated Dec. 28, 2021, 12 pages (6 pages of English Translation and 6 pages of Original Document).
Final Office Action issued in U.S. Appl. No. 16/584,517, dated May 18, 2022 with double-patenting rejections on pp. 18-25.
Notice of Allowance issued in U.S. Appl. No. 16/584,517, dated Sep. 14, 2022, 8 pages.

* cited by examiner

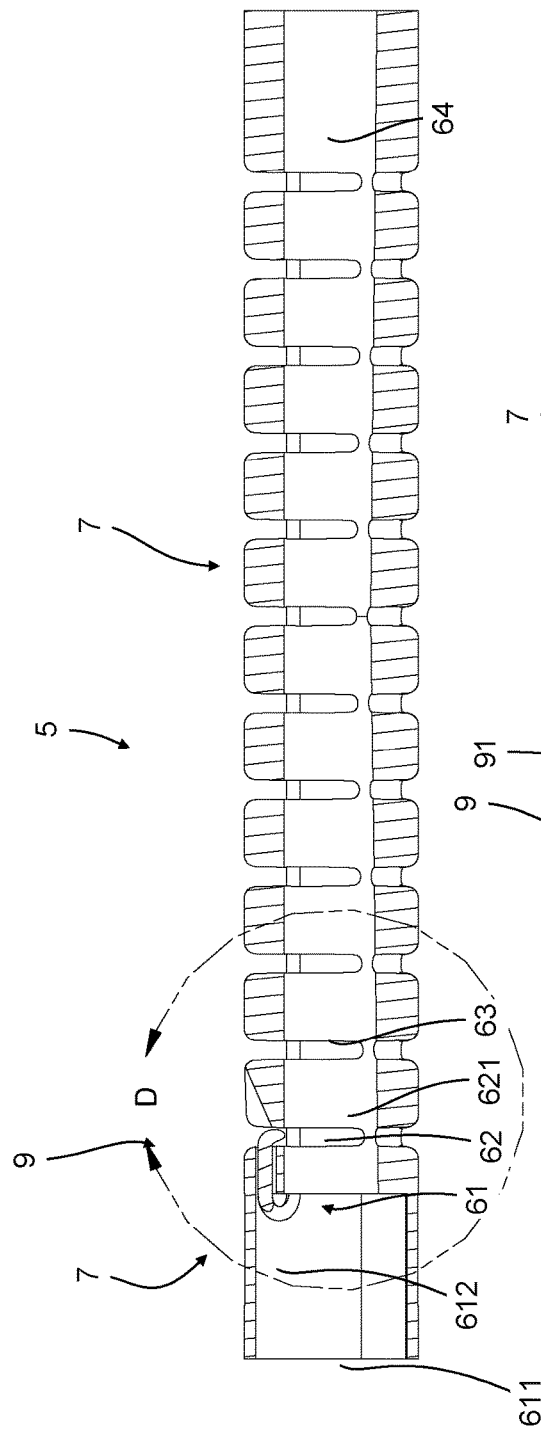
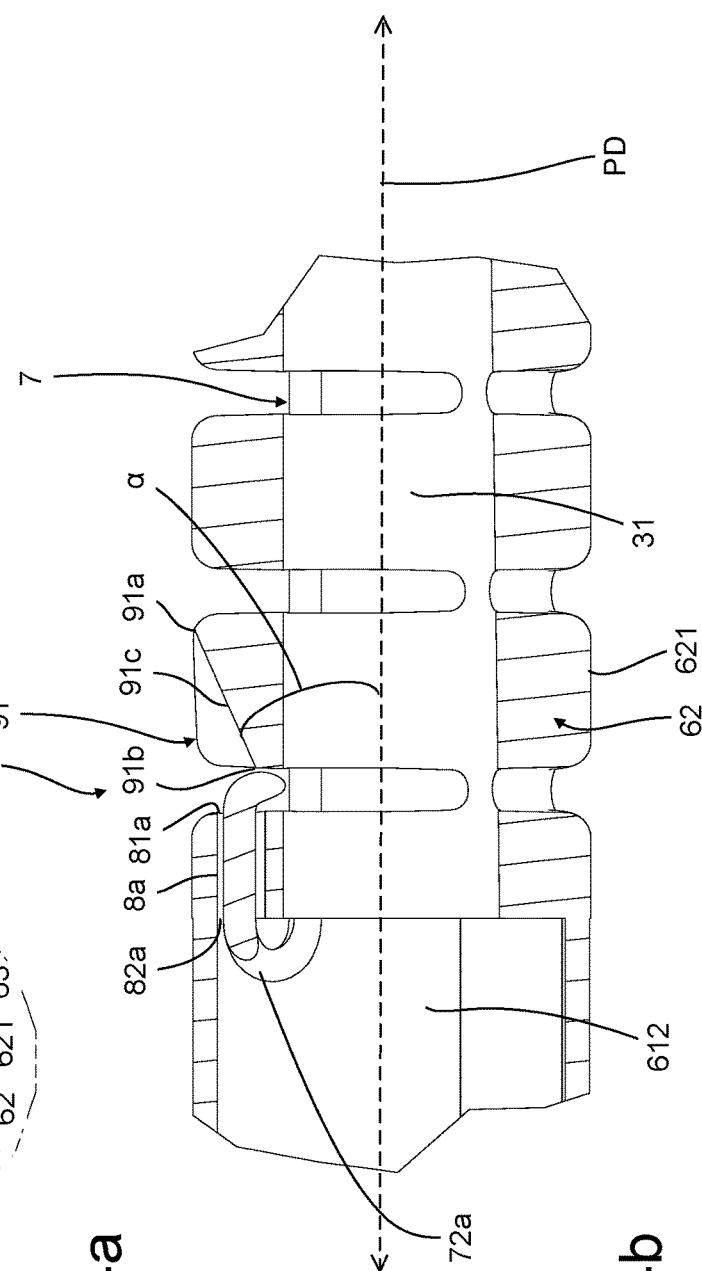
Fig. 4a
Fig. 4b

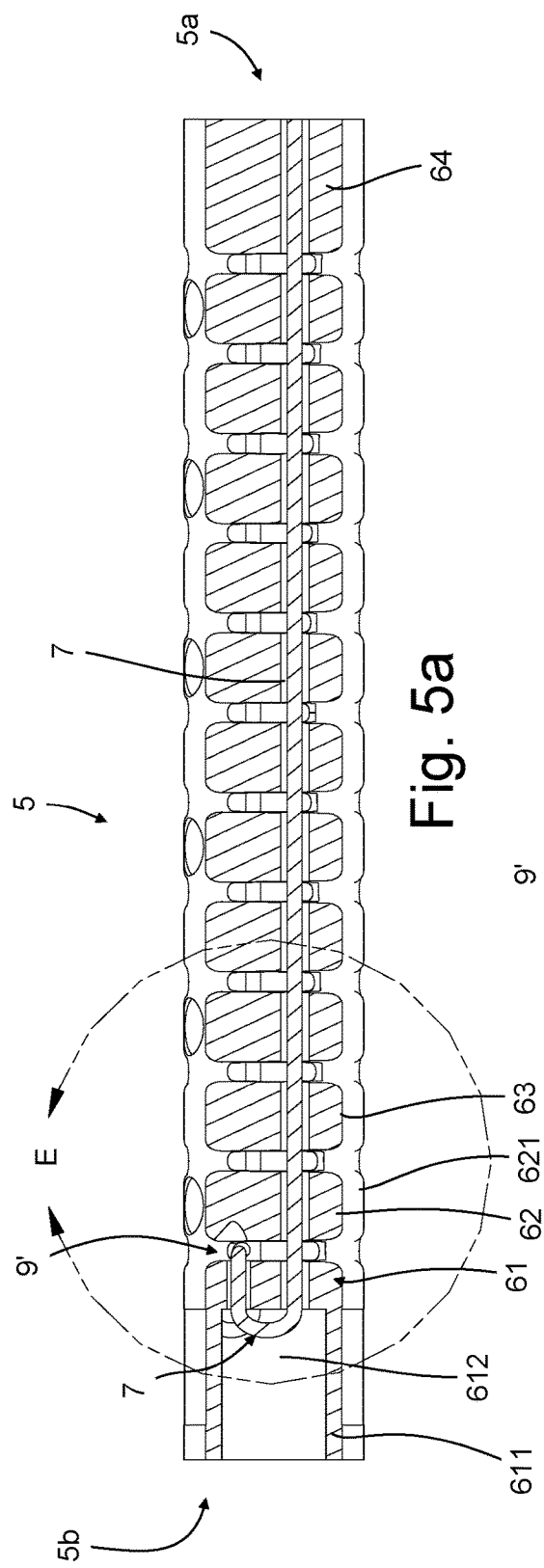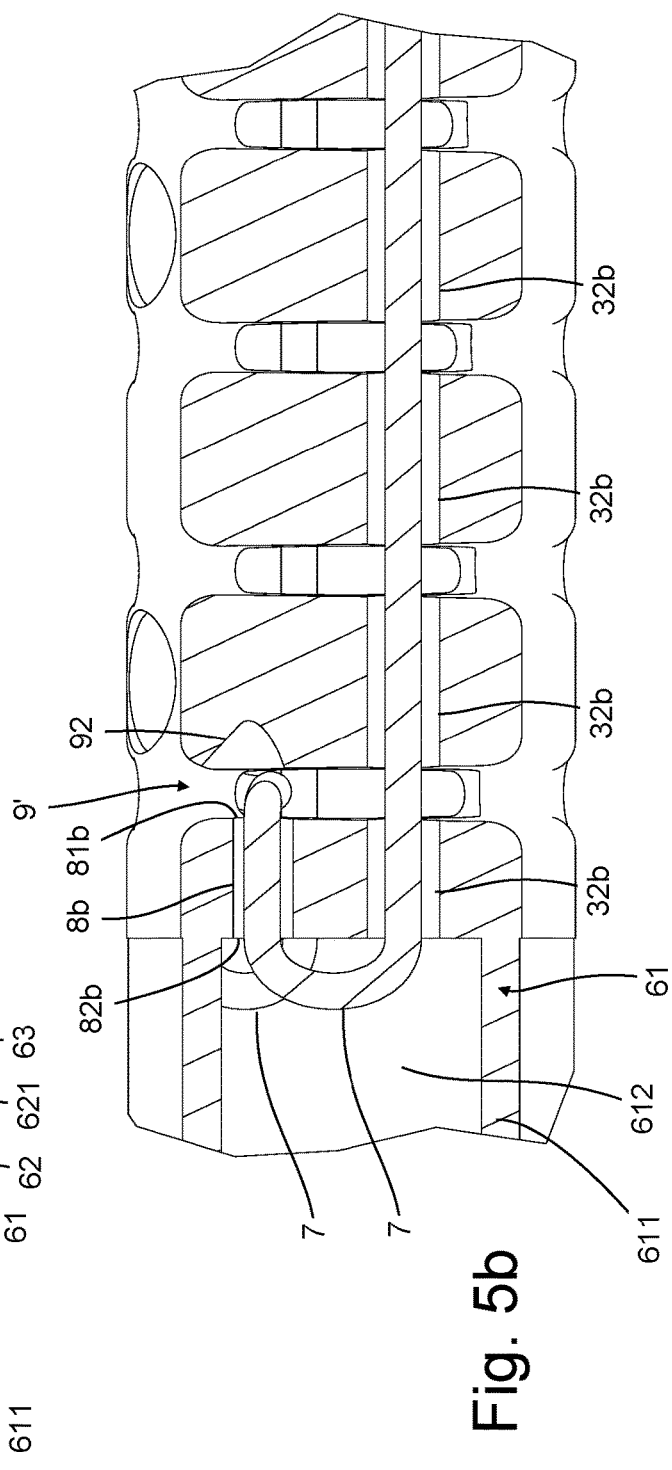

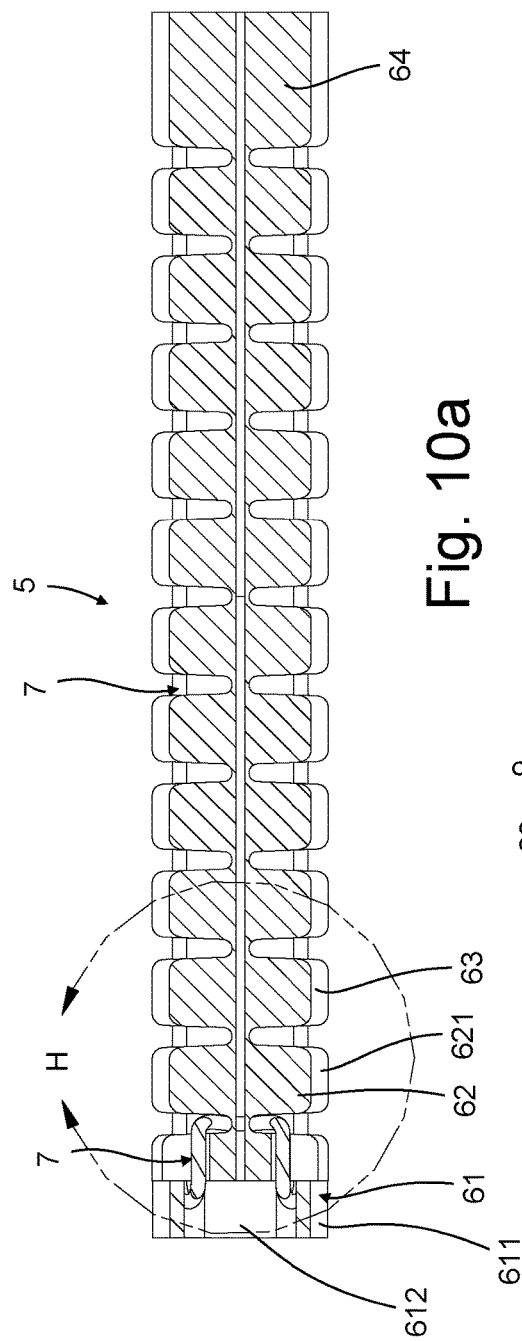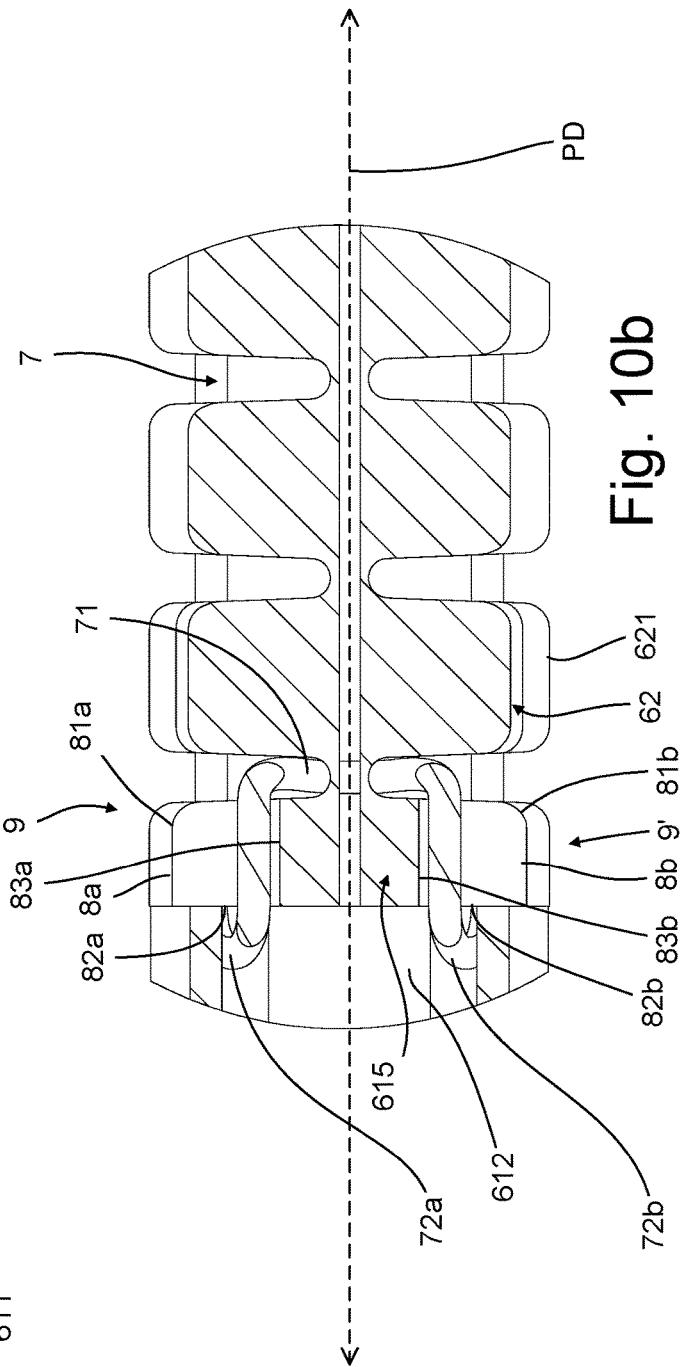

ARTICULATED TIP PART FOR AN ENDOSCOPE

CROSS-REFERENCE TO RELATED APPLICATIONS

This application claims priority from European Patent Application No. 18199998, filed Oct. 12, 2018, which application is incorporated herein by reference thereto.

TECHNICAL FIELD

The present disclosure relates to endoscopes, and more specifically to an articulated tip part for an endoscope.

BACKGROUND

Endoscopes are well known for visually inspecting inaccessible places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fibre, may provide illumination.

Electrical wiring for the camera and other electronics, such as LED lighting accommodated in the tip part at the distal end, run along the inside of the elongated insertion tube from the handle to the tip part. Instead of using cameras, endoscopes may also be fibre-optic, in which case the optical fibres run along the inside of the elongated insertion tube to the tip part. For some applications, a working or suction channel may run along the inside of the insertion tube from the handle to the tip part, e.g. allowing liquid to be removed from the body cavity or allowing for insertion of surgical instruments or the like, into the body cavity. The suction channel may be connected to a suction connector, typically positioned at a handle at the proximal end of the insertion tube. For other applications, the working or suction channel may be omitted.

In order to be able to manoeuvre the endoscope inside the body cavity, the distal end of the endoscope may comprise a bending section with increased flexibility, e.g. an articulated tip part allowing the operator to bend this section. Typically this is done by tensioning or slacking steering wires also running along the inside of the elongated insertion tube from the articulated tip part to a control mechanism of the handle.

An example of such an endoscope is disclosed in international patent publication WO 2014/106511 A1. This endoscope includes a bending section and a steering wire. The steering wire is secured to the distal end of the tip part so that once the steering wire is tensioned, the bending section of the tip part will bend towards the steering wire. This allows manoeuvering the endoscope inside the body cavity.

The steering wire of the prior art is usually secured in the distal end of the tip part by means of threading. One drawback is that threading requires a considerable amount of assembler dexterity which increases the assembly time, an important cost driver especially for single-use endoscopes.

A general desire in the field is to miniaturize the insertion tube of the endoscope, and thus the tip part, as this opens up new fields of application, for instance endoscopes for Ear, Nose, and Throat (ENT) endoscopy, such as rhinoscopy or rhinolaryngoscopy, which requires an insertion tube with a smaller footprint than for instance bronchoscopy. However, the drawbacks of threading are exacerbated when the endoscope is made smaller, since the bending section will be so small that threading passages may be difficult to see for an ordinary assembler.

SUMMARY

On this background, it may be seen as an object of the present disclosure to provide an improved articulated tip part for an endoscope.

One or more of these objects may be met by the present disclosure as described in the following.

An articulated tip part for an endoscope, an endoscope including the articulated tip part, and a method of assembling the articulated tip part and the endoscope are provided.

A first aspect of the disclosure relates to a bendable articulated tip part for an endoscope (hereafter the articulated tip part may also be referred to as the "tip part"), the articulated tip part comprising a number of hingedly connected segments including a distal end segment and a second segment, wherein adjacent segments are interconnected by at least one hinge member, whereby the tip part can be bent by means of the hingedly connected segments, and an insertion guide adapted for accommodating and guiding a steering wire and including an entry provided in an outer circumferential surface of the distal end segment or the second segment, and an exit leading to a spacing enclosed by an outer circumferential wall of the distal end segment, whereby an end of a steering wire can be guided into the spacing of the distal end segment via the entry of the insertion guide, wherein each segment comprises a proximal surface facing a distal surface of an adjacent segment forming a gap between them, and at least one hinge member bridges the gap, and wherein the entry of a distal portion of the first insertion guide is provided in the proximal surface of the distal end segment.

An advantage of a tip part according to the disclosure may be that threading one or more steering wires in the number of hingedly connected segments is made easier for the assembler of the tip part, since it has been experienced that positioning the end of a steering wire in an insertion guide is considerably easier than inserting the end in a hole of the distal end segment, especially if the hole does not have an opening in an outer circumferential surface.

An advantage of a tip part according to the disclosure may be that the provision of an insertion guide facilitates assembly of a steering wire by providing a visual indication for the method of assembly.

An advantage of a tip part according to the disclosure may be that the provision of an insertion guide reduces the dexterity required by the assembler.

An advantage of a tip part according to the disclosure may be that the tip part and/or the insertion tube can be made with a smaller footprint, e.g. a smaller diameter. The tip part may be made with a diameter of 3 mm or less. Prior art tubes are typically made with a diameter of 4 mm or greater. A smaller tip part may also allow using the tip part for other applications such as ear, nose, and throat endoscopy, e.g. rhinoscopy and/or rhinolaryngoscopy.

The tip part may extend along a proximal-distal axis. The proximal-distal axis may coincide with a centre line of the tip part. The proximal-distal axis is not necessarily always straight, since the tip part may bend, the proximal-distal axis may still coincide with the centre line of the tip part.

The second segment may be adjacent to the distal end segment. However, while advantageous, this is not strictly necessary as there could be one or more intermediate segments between the second segment and the distal end segment, and intermediate portions of the insertion guide, potentially formed by through holes, in these intermediate segments may allow direct alignment of portions of the insertion guide.

The second segment and the distal end segment may be interconnected by at least one hinge member. Additionally or alternatively, each pair of adjacent segments may be interconnected by at least one hinge member. Hinge member(s) may be bridging a gap between adjacent segments.

Each segment may comprise a proximal surface facing a distal surface of an adjacent segment forming a gap therein between, and at least one hinge member may bridge the gap. Each segment may comprise a distal surface facing a proximal surface of an adjacent segment forming a gap therein between, and at least one hinge member may bridge the gap. The proximal surface and/or distal surface of each segment may be substantially planar. The exit of the proximal portion of the first and/or the second insertion guide may be provided in the distal surface of the second segment, and the entry of the distal portion of the first and/or the second insertion portion may be provided in the proximal surface of the distal end segment.

Each segment may be provided with a similar, potentially equal, circumference. The segments may be substantially disc-shaped and/or cylindrically shaped. Each segment may be substantially cylindrical disc-shaped with an outer circumferential surface, so that the tip part has a uniform outer contour. The outer circumferential surface may extend around a proximal-distal axis of the tip part. The "outer circumferential surface" may be understood as an "outermost circumferential surface". It should also be understood that while the tip part may be cylindrically shaped, the features of the present disclosure are not limited to cylindrically shaped segments, therefore the circumferential surface or outer circumferential surface may more aptly be described as the outer surface, radially outwardly facing surface, or outermost surface, of the segments.

In this specification, the term "outer surface" may be understood as a surface intended to face, though not necessarily be exposed to, a body cavity when the tip part is inserted into a body. A sleeve or an external sheath may be provided over the outer surface of the tip part and/or the main tube. The sleeve may provide the tip part and/or the main tube with an outer surface which is suitable for exposure to body tissue.

The number of hingedly connected segments may form part of a bending section of the bendable articulated tip part. The bending section may be configured to be connected to a main tube of the endoscope at a proximal end thereof. The bending section may be configured to attach a camera assembly at a distal end thereof.

The tip part may comprise one or more light sources positioned at a distal end of the tip part so that light emitted from the light source is directed distally. The light source(s) may be light emitting diode(s) and/or light fibre(s).

The control element may be configured to allow an operator to control the tip part by the at least one steering wire. The control element may allow bending the tip part in at least one direction, potentially in two directions, the two directions potentially being opposite. The control element may be accommodated in an operating handle. The control element may include a lever allowing an operator to control the control element. The lever may extend outwardly from the control element, potentially through the operating handle. The control element may be in the form of a roller or a roller disc.

The operating handle may be suitable for allowing an operator to grip and to operate the endoscope, potentially with one hand. The operating handle may comprise a handle housing arranged at a proximal end of the insertion tube. The handle housing may accommodate the control element.

The tip part may form part of an insertion tube. The tip part may be positioned at a distal end of the insertion tube. The insertion tube may be suitable for insertion into a body cavity, potentially a lung, through a body opening, potentially a mouth, nose, and/or ear. The body may be a natural and/or artificial body, potentially a human body. The insertion tube may extend from the operating handle towards a distal end of the endoscope. The insertion tube may comprise a main tube connected to a proximal end of the tip part.

A sleeve or an external sheath may enclose the tip part and/or the main tube. The sleeve or external sheath may seal the connection between the tip part and the main tube. The sleeve or external sheath may provide the tip part and/or the main tube with an outer surface which is suitable for insertion into a body cavity, e.g. a smooth outer surface.

The tip part may comprise a camera assembly positioned at a distal end of the tip part and allowing an operator to inspect a body cavity, when the tip part is inserted into the body cavity. The camera assembly may comprise one or more selected from the group consisting of: an image sensor configured to capture an image, at least one lens configured to alter light received by the image sensor, a camera housing for supporting the parts of the camera assembly, at least one light source configured to provide illumination for the image sensor, a printed circuit board, at least one signal cable for carrying an image signal from the camera assembly to the operator, and a power cable for supplying the camera assembly with electricity. The printed circuit board may be configured to process a signal from the image sensor. The signal cable and/or the power cable may be connected to printed circuit board. The power cable may be configured to supply power to the printed circuit board.

The segments may comprise at least one cable passage for accommodating at least one cable, e.g. a signal cable for carrying an image signal and/or a power cable for carrying electricity. The cable passage may comprise a through hole in each of the segments, potentially so as to form a cable passage extending from the distal end segment through the intermediate segment(s) to the proximal end segment. The cable passage may be positioned in a centre of the segments. The tip part may comprise a signal cable for carrying an image signal and/or a power cable for carrying electricity positioned in the cable passage.

The tip part may comprise a working passage. The working passage may be configured for accommodating a tube providing a working channel. The working channel may be a suction channel for providing a suction at the distal end of the tip part. The suction channel may be connected to a suction connector, potentially at a handle at the proximal end of the insertion tube. The working channel may allow insertion of surgical instruments there through to the distal end of the tip part. The working passage may be omitted to minimize the size of the tip part.

The insertion guide may be provided so that when a steering wire is secured in the insertion guide, the steering wire is positioned more centrally compared to the outer surface of the circumferential wall of the distal end segment. Potentially so that the outer circumference of the tip part is unchanged or so that the steering wire is positioned below the outer circumference of the tip part after assembly of the steering wire.

The insertion guide may be a first insertion guide. The bendable articulated tip part may comprise a second insertion guide adapted for accommodating and guiding a steering wire and including an entry provided in an outer circumferential surface of the distal end segment or the second segment, and an exit leading to the spacing enclosed by the outer circumferential wall of the distal end segment, whereby an end of a steering wire can be guided into the spacing of the distal end segment via the entry of the second insertion guide. The second insertion guide may be provided similarly to the first insertion guide. The second insertion guide may be provided so as to mirror the first insertion guide.

Additionally or alternatively, the insertion guide is formed by a recess in the outer circumferential surface of the distal end segment or the second segment.

The first and/or second insertion guide, potentially a proximal portion of the first and/or second insertion guide, may be provided as a first and/or second through hole, respectively.

Additionally or alternatively, the number of hingedly connected segments may comprise a plurality of intermediate segments, wherein the plurality of intermediate segments may include the second segment, and wherein adjacent segments may be interconnected by at least one hinge member.

Additionally or alternatively, the number of hingedly connected segments may comprise a proximal end segment configured for connection with the remaining parts of the endoscope, potentially a main tube of the endoscope.

Additionally or alternatively, the insertion guide may comprise a distal portion provided in the distal end segment and a proximal portion provided in the second segment, wherein the entry of the insertion guide is provided by an entry of the proximal portion in the outer circumferential surface of the second segment, whereby an end of a steering wire can be guided into the spacing of the distal end segment via the entry of the proximal portion through to the exit of the distal portion.

This may provide the advantage that the insertion guide may be made longer, so as to further facilitate assembly of a steering wire.

The insertion guide may be arranged with a gap between the exit of the proximal portion and the entry of the distal portion.

Additionally or alternatively, a portion, potentially the distal portion, of the insertion guide may be formed by a through hole provided in the distal end segment, wherein the exit of the insertion guide is provided by an exit of the through hole. The entry of the insertion guide may be provided a portion, potentially the proximal portion, of the insertion guide, potentially formed as a recess in the outer circumferential surface of the second segment.

This may provide the advantage that, after assembly, the steering wire may be positioned enclosed in the distal portion of the insertion guide, which may be advantageous regarding electrical insulation of the steering wire.

Additionally or alternatively, an exit of the proximal portion may be aligned with an entry of the distal portion, whereby an end of a steering wire can be guided into the entry of the distal portion and onto the spacing of the distal end segment via the proximal portion of the insertion guide.

This may provide the advantage that the threading of the steering wire is further facilitated in that the end of the steering wire may be guided by both the proximal portion and the distal portion.

Additionally or alternatively, an exit of the proximal portion and an entry of the distal portion are arranged with a gap therein between, wherein the distal portion and the proximal portion are arranged so that an end of a steering wire can be guided over the gap and into the spacing of the distal end segment via the entry of the insertion guide. The gap may be bridged by at least one hinge member.

Additionally or alternatively, the insertion guide may form a duct.

This may provide the advantage that threading the wire is further facilitated.

Additionally or alternatively, the proximal and/or distal portion of the insertion guide may be formed by a recess, a trough, a hole, a notch, and/or a slit. The proximal segment, may be formed by a hole through the second segment with an entry opening in the outer circumferential surface and an exit opening, potentially in a distal surface of the second segment and potentially aligned with the entry of the distal portion of the insertion guide.

Additionally or alternatively, the insertion guide, potentially a bottom of the proximal portion of the insertion guide, may form a ramp.

This may provide the advantage that the end of the steering wire may increasingly be predisposed for being guided through the insertion guide into the spacing of the distal end segment, since the ramp can be adjusted to correspond to the predominant insertion angle of the assembler.

The ramp may taper off towards a distal end of the tip part. The ramp may taper off from the entry of the insertion guide, potentially the entry of the proximal portion of the insertion guide, to the exit of the insertion guide, potentially the exit of the proximal portion of the insertion guide. The entry of the insertion guide, potentially the entry of the proximal portion of the insertion guide, may be arranged flush with the outer circumferential surface of the second segment. The entry and exit of the insertion guide may be arranged along the proximal-distal axis. The ramp or the bottom of the insertion guide may form an angle in relation to the proximal-distal axis, potentially in relation to a centre line of the second segment. The angle may potentially be in the range of 15°-45°, in the range of 20°-40°, or preferably about 30°. This has been found to potentially improve the success rate of guiding the steering wire through the insertion guide.

Additionally or alternatively, the at least one hinge member may be a film hinge and/or an integral hinge and/or a living hinge.

This may provide the advantage, that these hinge types are easy to form simultaneously with forming the insertion guide. This may especially be the case if the tip part is moulded in one piece.

The at least one hinge member may alternatively be any other suitable hinge type.

Additionally or alternatively, the number of hingedly connected segments may comprise a steering wire passage, potentially having a through hole in the distal end segment and/or in each of the number of hingedly connected segments.

The steering wire passage may be configured to enclose or surround a steering wire positioned therein.

The steering wire passage may be substantially straight, potentially when the tip part is in an unbent or resting position. The trough holes of the steering wire passage may be positioned to enclose a straight line, potentially when the tip part is in an unbent or resting position.

The steering wire passage may be a first steering wire passage and the number of hingedly connected segments may comprise a second steering wire passage, potentially having a through hole in the distal end segment or in each of the number of hingedly connected segments. The second steering wire passage may be provided similarly to the first steering wire passage. The through holes of the second steering wire passage may be different from the through holes of the first steering wire passage. The first steering wire passage and the second steering wire passage may be symmetrically positioned, potentially on opposite sides of the number of hingedly connected segments.

Additionally or alternatively, the distal end segment, the at least one hinge member, and the second segment may be integrally formed in one piece. The number of hingedly connected segments or the bending section may be integrally formed in one piece.

Additionally or alternatively, the outer circumferential surface of each hingedly connected segment may be substantially cylindrically shaped, so that the tip part may have a uniform outer contour.

The outer circumferential surface of each segment may extend around the proximal-distal axis of the tip part.

Additionally or alternatively, the articulated tip part may comprise a steering wire positioned in the insertion guide, potentially in the distal portion of the insertion guide.

The steering wire may further be positioned in the steering wire passage. The steering wire may be secured to the distal end of the tip part, potentially to the distal end segment, by means of a friction engagement. At least one end, potentially two ends, of the steering wire may be connected to the control handle, potentially to the control lever of the control handle, whereby the movement of the control handle causes the articulated tip part to bend. Thus by manipulating the control element the steering wire may be tensioned on one side of the plane of the hinge members, and slacked on the other, thus allowing the bending section or tip part to bend in a desired direction.

The steering wire may be a first steering wire and the articulated tip part may further comprise a second steering wire, potentially provided similarly to the first steering wire. The second steering wire may be positioned in the second steering wire passage.

Additionally or alternatively, a section, potentially an intermediate or middle section, of the steering wire may be secured at the distal end of the tip part by means of a friction engagement.

A friction engagement may be a particularly simple way of securing the steering wire.

The friction engagement may be formed by at least one, potentially at least two, or potentially three, bend(s) of the steering wire. The bend(s) may be provided at the distal end segment.

Additionally or alternatively, the tip part may form part of an endoscope and may be positioned at a distal end of the endoscope.

Additionally or alternatively, the endoscope may form part of a system for visually inspecting inaccessible places such as human body cavities, the system further comprising a monitor. The endoscope may be connectable to the monitor, and the monitor may allow an operator to view an image captured by the camera assembly of the endoscope.

A second aspect of the disclosure relates to a use of an articulated tip part according to the first aspect of the disclosure. The articulated tip part may be used as a part of an endoscope, potentially for Ear, Nose, and Throat (ENT) endoscopy, such as rhinoscopy or rhinolaryngoscopy.

A third aspect of the disclosure relates a method for guiding a steering wire in an articulated tip part for an endoscope according to the first aspect of the disclosure, the method may comprise a step of guiding an end of a steering wire into the spacing of the distal segment via the entry of the insertion guide.

An advantage of a method according to the disclosure may be that threading one or more steering wires in the number of hingedly connected segments is made easier for the assembler of the tip part.

An advantage of a method according to the disclosure may be that the provision of an insertion guide facilitates assembly of a steering wire by providing a visual indication for the method of assembly.

The method may comprise a step, potentially performed prior to the step of guiding an end of a steering wire into the spacing of the distal segment via the entry of the insertion guide, of inserting an end of the steering wire between two adjacent segments of the tip part. At least one, potentially both, of the adjacent segments may comprise the insertion guide. The two adjacent segments may be the distal end segment and the second segment. The end of the steering wire may potentially be inserted in a gap between two hinge member connecting the two adjacent segments.

The method may comprise a step of guiding another end of the steering wire into second, different insertion guide via an entry of the second insertion guide. The steering wire may thus form an intermediate bend from the first insertion guide to the second insertion guide.

The method may comprise a step of guiding the first and/or the second end of the steering wire through a respective first and/or second steering wire passage.

A person skilled in the art will appreciate that any one or more of the above aspects of the disclosure and embodiments thereof may be combined with any one or more of the other aspects of the disclosure and embodiments thereof.

BRIEF DESCRIPTION OF DRAWINGS

The invention will now be described in greater detail based on non-limiting exemplary embodiments and with reference to the drawings, on which:

FIG. 4a shows a cross-sectional view of the tip part along the line B-B of FIG. 3a, FIG. 4b shows detail view D of the tip part shown in FIG. 4a, FIG. 5a shows a cross-sectional view of the tip part along the line C-C of FIG. 3a, FIG. 5b shows detail view E of the tip part shown in FIG. 5a, FIG. 6 shows a perspective view of a section of the first embodiment of the tip part prior to being threaded, FIG. 10a shows a cross-sectional view of the tip part along the line F-F of FIG. 9a, FIG. 10b shows detail view H of the tip part shown in FIG. 10a, FIG. 11a shows a perspective view of the tip part shown in FIG. 9b, in which intermediate segments of the tip part are omitted.

DETAILED DESCRIPTION

Figure 1A:
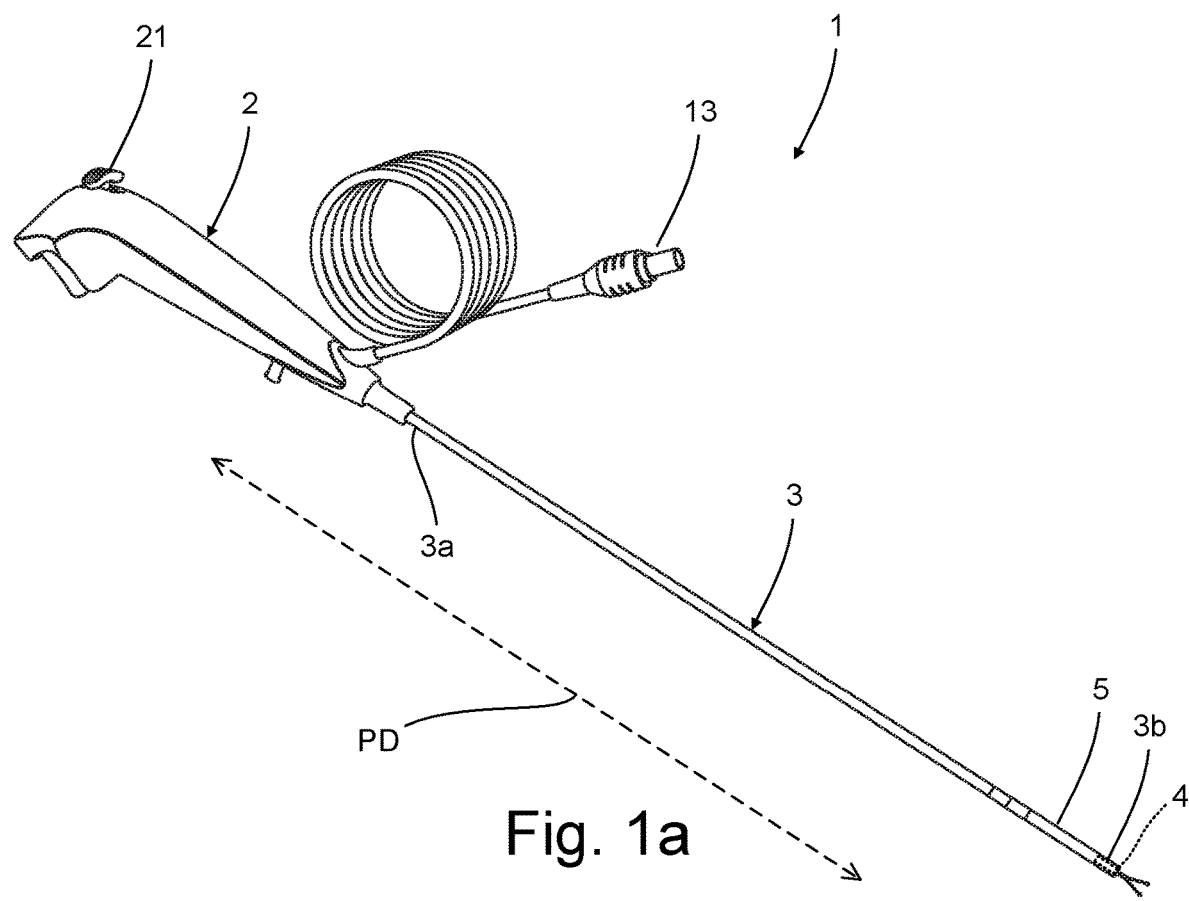
FIG. 1a shows a perspective view of an endoscope in which a tip part according to the present disclosure is implemented.

Referring first to FIG. 1a, an endoscope 1 is shown. The endoscope is disposable, and not intended to be cleaned and reused. The endoscope 1 comprises an elongated insertion tube 3. At the proximal end 3a of the insertion tube 3 an operating handle 2 is arranged. The operating handle 2 has a control lever 21 for manoeuvering an articulated tip part 5 at the distal end 3b of the insertion tube 3 by means of a steering wire 7 (visible in FIG. 2a). A camera assembly 4 is positioned in the tip part 5 and is configured to transmit an image signal through a monitor cable 13 of the endoscope 1 to a monitor 11.

Figure 1B:
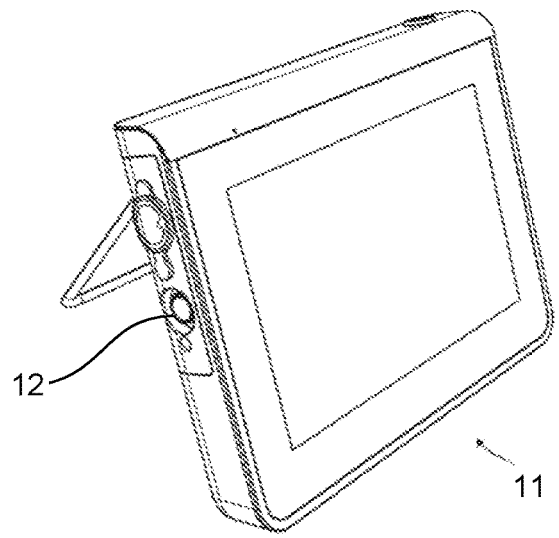
FIG. 1b shows a perspective view of a monitor operable to present images obtained with the endoscope of FIG. 1a, FIG. 2a shows a side view of an insertion tube in which a tip part according to a first embodiment of the present disclosure is implemented.

In FIG. 1b, the monitor 11 is shown. The monitor 11 may allow an operator to view an image captured by the camera assembly 4 of the endoscope 1. The monitor 11 comprises a cable socket 12 to which a monitor cable 13 of the endoscope 1 can be connected to establish a signal communication between the camera assembly 4 of the endoscope 1 and the monitor 11.

Figure 2A:
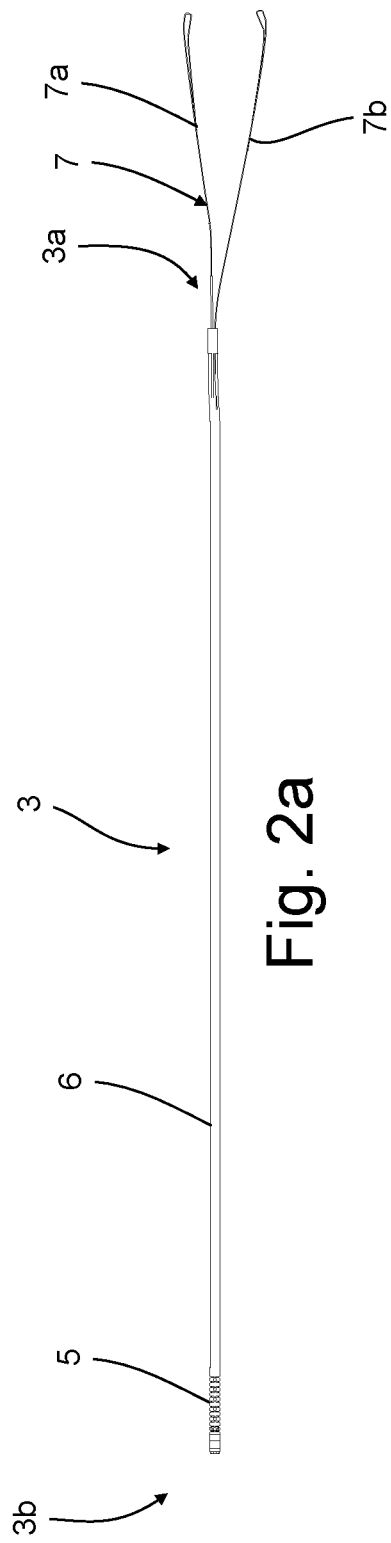
FIG. 2b shows a side view of a section of a tip part according to the first embodiment of the present disclosure.

Turning now to FIG. 2a, details of the insertion tube 3 are shown. The insertion tube comprises the articulated tip part 5 positioned at the distal end 3b of the insertion tube 3. A proximal end of the tip part 5 is connected to a main tube 6. Some parts, such as an external sheath or sleeve normally covering and sealing the connection between the articulated tip part 5 and the main tube 6, have been removed for clarity. A steering wire 7 runs inside the main tube 6 and the tip part 5, so that both ends extend from the proximal end 3a of the insertion tube 3. An intermediate section of the steering wire 7 is secured at the distal end of the tip part 5, so that one half of the steering wire 7 runs along one side of the tip part 5 and another half of the steering wire 7 runs along another, opposite side of the tip part 5. The two free ends 7a, 7b of the steering wire 7 are, in the assembled endoscope, connected to a control lever 21 of the operating handle 2. Thus, by manipulating the control lever 21 the steering wire 7 may be tensioned on one side of tip part 5, and slacked on the other, thus allowing the tip part 5 to bend in a desired direction.

Figure 2B:
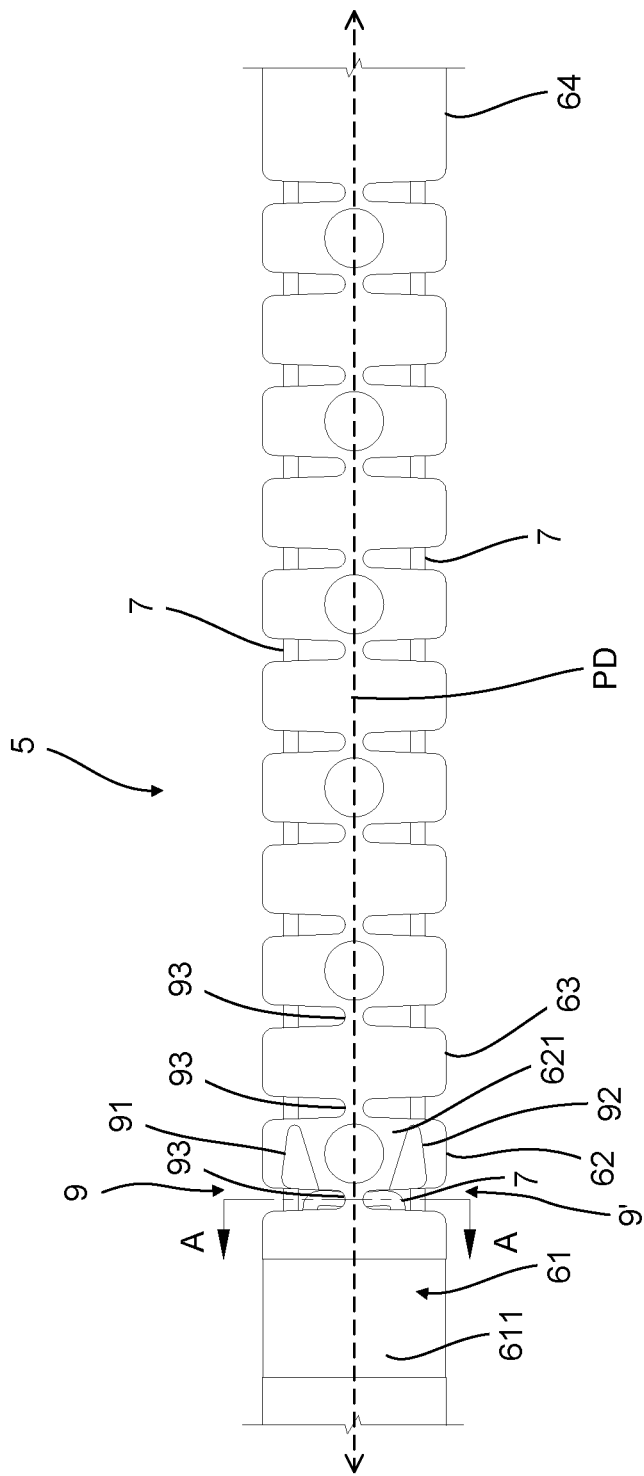

Turning to FIG. 2b, the articulated tip part 5 comprises a number of segments 61, 62, 63, 64. More specifically a distal end segment 61, a proximal end segment 64 for connection to the main tube 6 of the insertion tube 3, and a number of intermediate segments 62, 63. One of the intermediate segments, e.g. intermediate segment 62, may also be referred to as the "second segment". Only the two intermediate segments 62, 63 adjacent to the distal end segment 61 are marked with reference numerals, however the remaining intermediate segments are provided substantially equally. In the illustrated embodiments, the number of intermediate segments 62, 63 is eleven, but the skilled person will understand that the precise number is less important. Each segment is substantially cylindrical disc-shaped with an outer circumferential surface, so that the tip part 5 has a uniform outer contour. A proximal-distal axis PD coincides with a centre line extending through the centre of each segment 61, 62, 63, 64 of the tip part 5. Each intermediate segment comprises a proximal substantially planar surface facing a substantially planar distal surface of an adjacent segment forming a gap therein between, and a substantially planar distal surface facing a substantially planar proximal surface of an adjacent segment forming a gap therein between. As also shown in FIG. 3b, each gap is bridged by two flexible hinge members 93 positioned near the circumference of the tip part 5, so as allow the tip part 5 to bend.

The distal end segment 61, the intermediate segments 62, 63, the proximal end segment 64, and the hinge members 93 interconnecting the segments are integrally formed in one piece.

FIG. 2b shows the first embodiment of the tip part 5. In this embodiment, the tip part 5 comprises a first insertion guide 9 and a second insertion guide 9'. The first insertion guide 9 comprises a proximal portion 91 formed as a recess in an outer circumferential surface 621 of the second segment 62 and a distal portion 8a (best seen in FIGS. 3a and 3b) formed as a through-hole in a proximal wall 615 of the distal end segment 61. The second insertion guide 9' comprises a proximal portion 92 formed as a recess in the outer circumferential surface 621 of the second segment 62 and a distal portion 8b (best seen in FIGS. 3a and 3b) formed as a through-hole in the proximal wall 615 of the distal end segment 61.

Figure 3A:
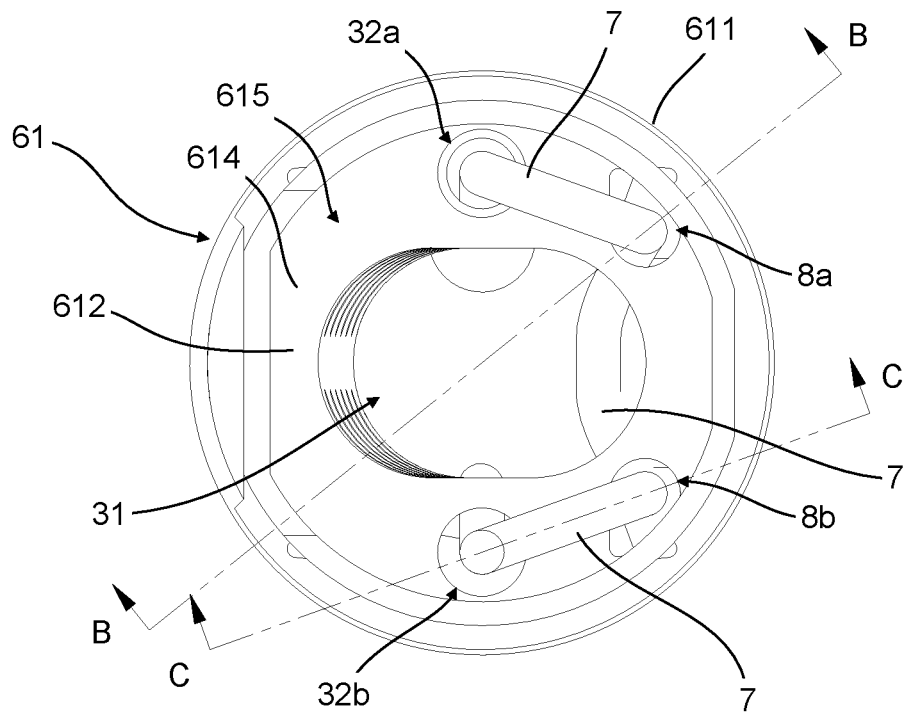
FIG. 3a shows a front view of the first embodiment of the tip part in which a camera assembly is omitted.
Figure 3B:
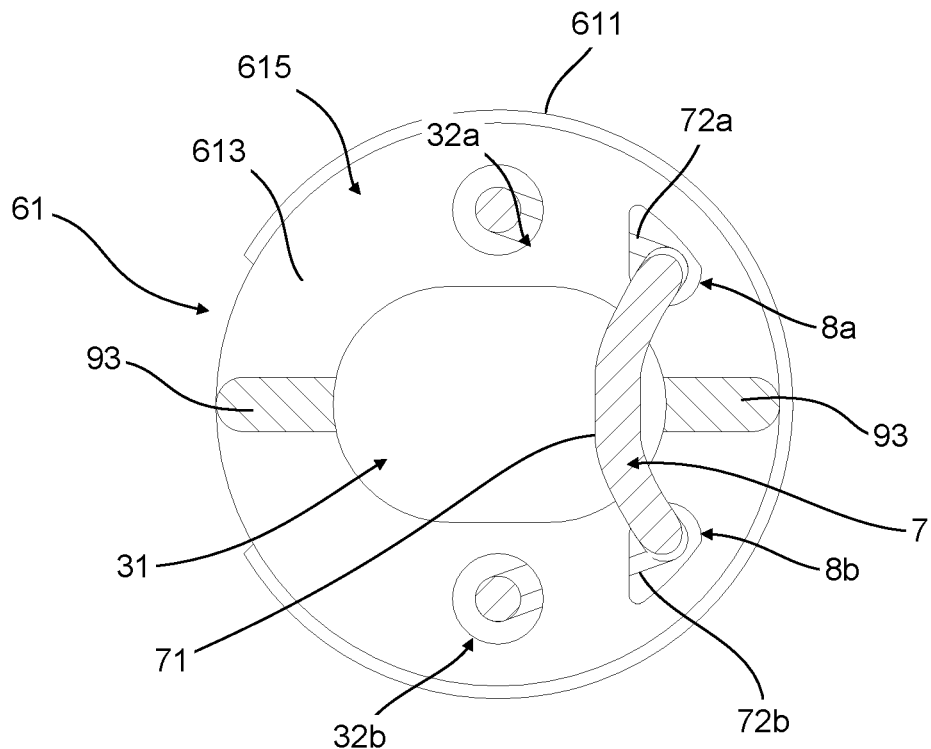
FIG. 3b shows a cross-sectional view of the tip part along the line A-A of FIG. 2b.

Turning now to FIG. 3a, the distal end segment 61 has a circumferential wall 611 enclosing a spacing 612. Normally, the distal end segment 61 comprises a camera assembly with an image sensor and light emitting diodes positioned in the spacing 612, however in these figures the camera assembly has been omitted for clarity. The distal end segment 61 has a circumferential wall 611 enclosing a spacing 612, a first distal portion 8a, and a second distal portion 8b. The first and second distal portions 8a, 8b are in the form of through holes and have an entry 81a, 81b in the proximal surface 613 of the distal end segment 61 and an exit 82a, 82b in the distal surface 614 of the proximal wall 615 leading to the spacing 612 of the distal end segment 61, as seen in FIGS. 3b, 4b.

The segments 61, 62, 63, 64 comprise a cable passage 31, a first steering wire passage 32a, and a second steering wire passage 32b. The cable passage 31 can be seen in FIGS. 4a-4b and is for accommodating a signal cable for carrying an image signal from a camera assembly (not shown) incorporated in the distal end segment 61 and a power cable for carrying electricity to the camera assembly. The second steering wire passage 32b can be seen in FIG. 5a-5b, however the first steering wire passage 32a is provided substantially equally. The steering wire passages 32a, 32b are for accommodating the steering wire 7 and for securing that the steering wire 7 in the passages 32a, 32b does not move transversely in relation to the tip part 5. The cable passage 31 and the steering wire passages 32a, 32b are formed by aligned through holes provided in each segment, so as to form three separate, passages 31, 32a, 32b extending from the distal end segment 61 through the intermediate segments 62, 63 to the proximal end segment 64. The passages 31, 32a, 32b are straight when the tip part 5 is in a relaxed state. The cable passage 31 is provided along a centre of each segment, and the steering wire passages 32a, 32b are provided symmetrically on opposite sides of the cable passage 31.

As seen in FIG. 3b, each of the intermediate segments 62, 63 are interconnected with adjacent segments by the means of two flexible hinge members 93 arranged symmetrically on opposite sides in proximity to the circumference of the tip part 5. This type of hinge member may be known as a film hinge, an integral hinge, or a living hinge, however other types of hinges may be suitable.

Turning to FIGS. 4a and 4b showing details of the first insertion guide 91, however the second insertion guide 92 is provided substantially equally to the first insertion guide 91. Each of the proximal portions 91, 92 has an exit 91b aligned with an entry 81a, 81b of the respective distal portion 8a, 8b. The proximal portions 91, 92 are each provided as a recess with a bottom 91c forming a ramp which tapers off from the entry 91a of each proximal portion 91, 92 towards the exit 91b of each proximal portion 91, 92. The entry 91a of each proximal portion 91, 92 are arranged flush with the outer circumferential surface 621 of the second segment. The bottom 91c of each proximal portion 91, 92 forms an angle α with the proximal-distal axis PD of about 30°.

Figure 6:
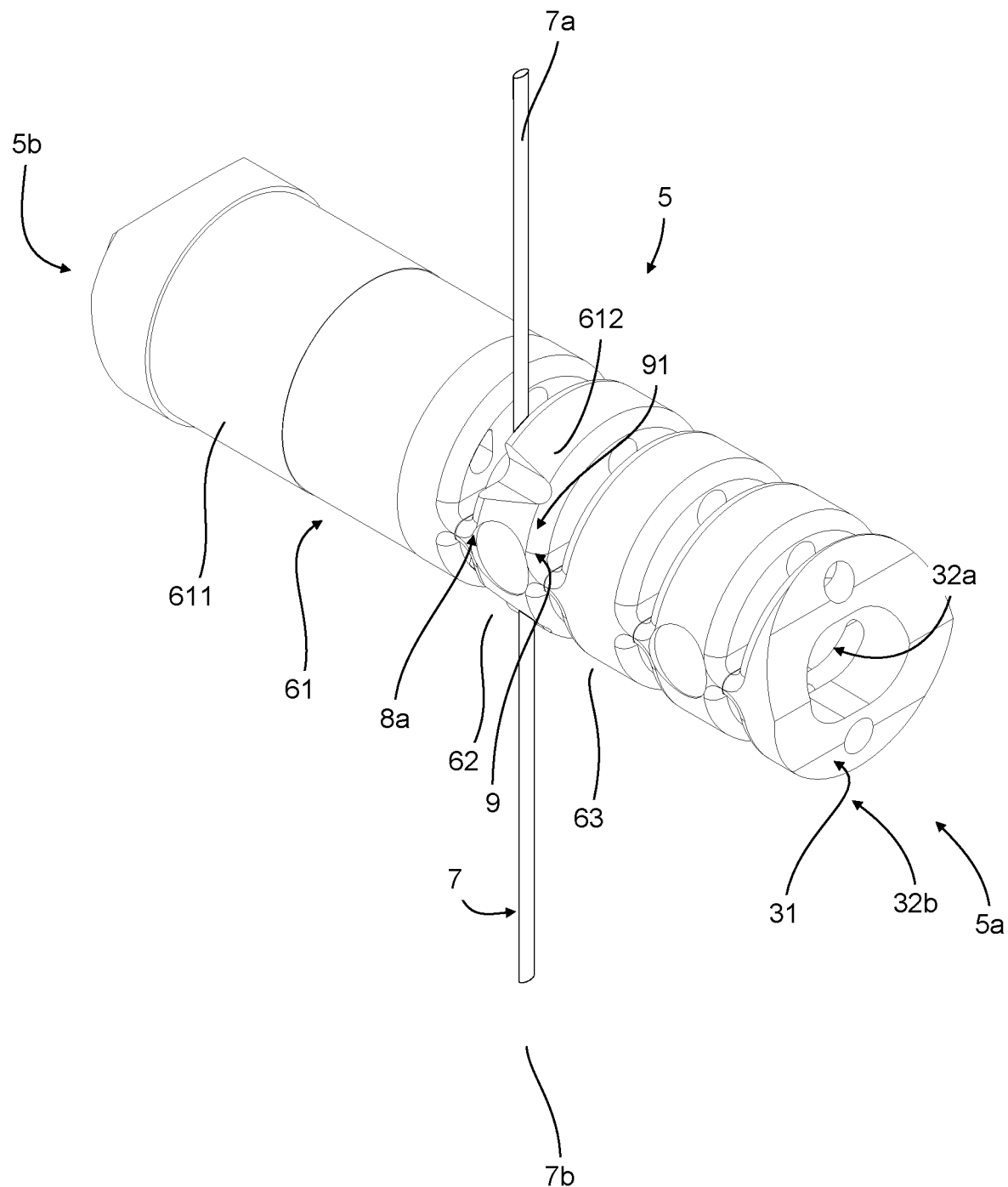
Figure 7:
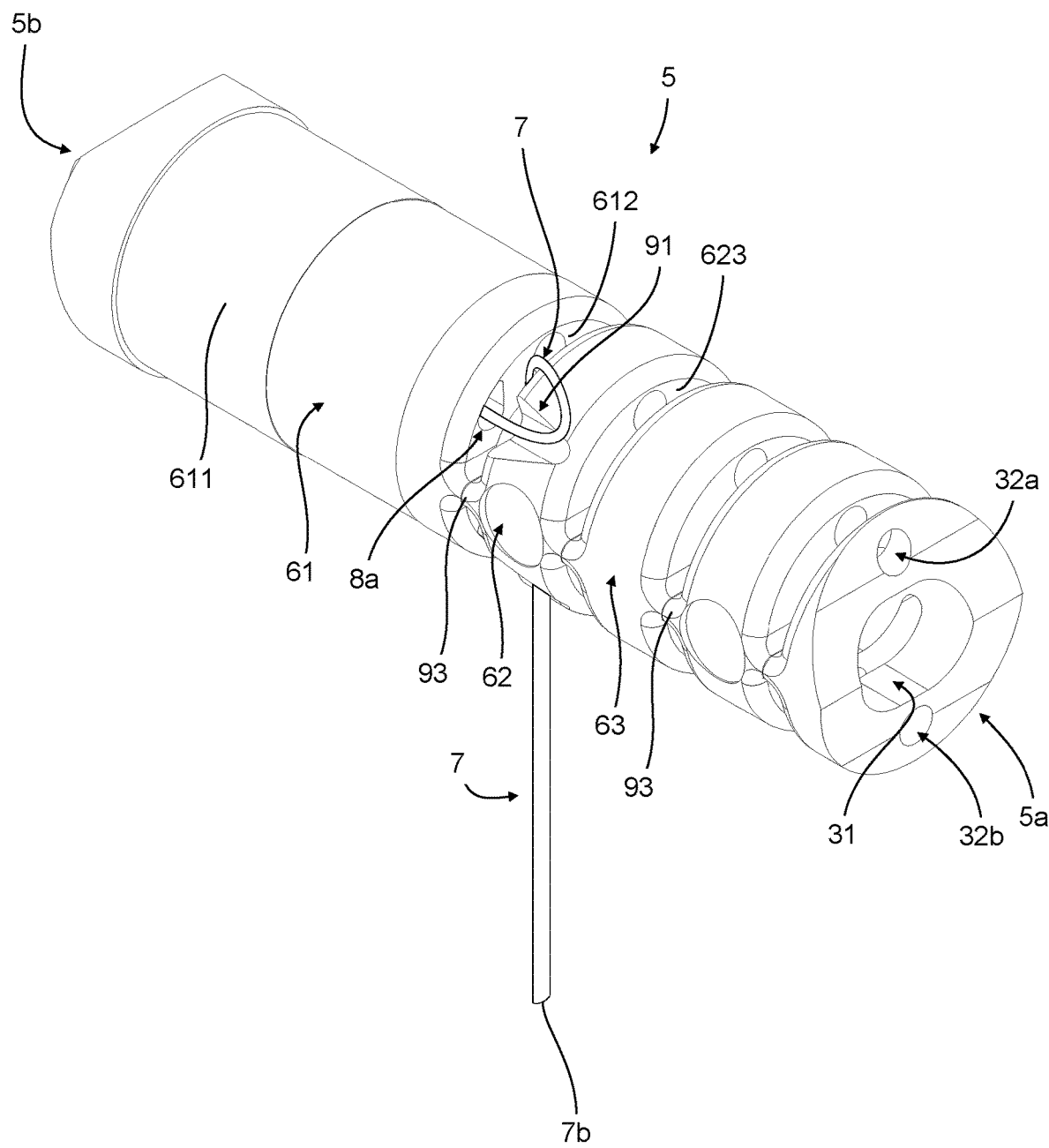
FIG. 7 shows a perspective view of a section of the first embodiment of the tip part being partially threaded.
Figure 8:
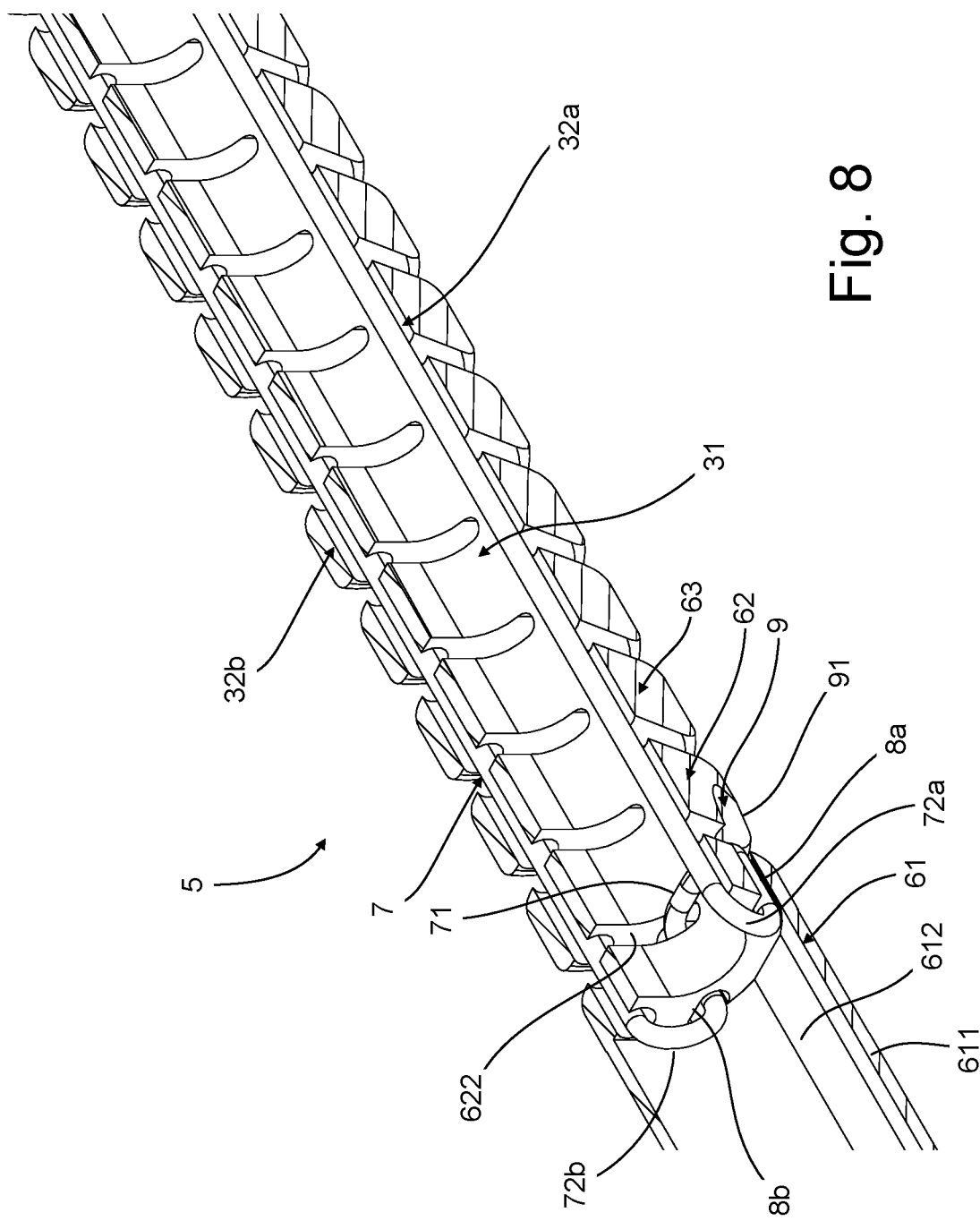
FIG. 8 shows a perspective view of a section of the first embodiment of the tip part after being threaded, wherein sections of the tip part omitted for visualization purposes.

In the following, a method of securing a steering wire 7 in a tip part 5 according to the first embodiment will be described, wherein the steps of the method are performed sequentially. Firstly, the steering wire 7 and a tip part 5 is provided. Secondly, as can be seen in FIG. 6, the steering wire 7 is positioned so that extends through a gap formed by the distal end segment 61, the second segment 62, and the two hinge members 93 interconnecting the distal 61 and second segment 62, and so that a first end 7a of the steering wire 7 extends on one side of the tip part 5, shown as above the tip part 5 on the FIG. 6, and a second end 7b of the steering wire 7 extends on another, different side of the tip part 5, shown as below the tip part 5 on FIG. 6. Thirdly, the first end 7a of the steering wire is guided by inserting it into the entry 91a of the proximal portion 91 of the first insertion guide 9 and sliding the first steering wire end 7a along the bottom 91c of the proximal portion 91, and until the first steering wire end 7a exits the proximal portion 91 through the exit 91b thereof. As the steering wire 7 is pushed further, the first steering wire end 7a will enter the entry 81a of the distal portion 8a of the first insertion guide 9 to arrive at the arrangement shown in FIG. 7. The step is then repeated for second end 7b of the steering wire 7, so that the ends 7a, 7b of the steering wire 7 extend through the respective distal portion 8a, 8b, and into the spacing 612 of the distal end segment 61, so that the steering wire 7 forms an intermediate steering wire bend 71 in the gap between the distal end segment 61 and the second segment 62. The steering wire bend 71 is positioned between the hinge members 93 and abutting one of the two hinge members 93. Fourthly, the ends 7a, 7b of the steering wire 7 is guided through the respective steering wire passages 32a, 32b, so that the ends of the steering wire 7a, 7b extend from the proximal end segment 64 arriving at the arrangement shown in FIG. 8, and so that the steering wire 7 forms a first steering wire bend 72a between the first distal portion 8a and the first steering wire passage 32a, and a second steering wire bend 72b between the second distal portion 8b and the second steering wire passage 32b. This ensures that the steering wire 7 is secured to the distal end segment 61 of the tip part 5 by a friction engagement, which prevents the steering wire 7 from sliding in the distal portions 8a, 8b when an end of the steering wire 7 is pulled. The tip part 5 can then be attached to the remaining parts of the insertion tube 3 and the endoscope 1.

The second embodiment of the tip part 5 is shown in FIGS. 9a to 11b. In the second embodiment, the insertion guides 9, 9' (also referred to in this embodiment as the insertion guide and the second insertion guide) do not comprise proximal portions 91, 92 as provided in the first embodiment. Instead, the insertion guides 9, 9' each comprise a distal portion 8a, 8b (also referred to in this embodiment as the insertion guide and the second insertion guide) formed as a recess provided in the outer circumferential surface 611 of the distal end segment 61 as best seen in FIGS. 9b, 10b, and 11a. The distal portions 8a, 8b each comprise an entry 81a, 81b provided in the proximal surface 613 and the outer circumferential surface 611 of the distal end segment 61, and an exit 82a, 82b in the distal surface 614 of the proximal wall 615, leading to the spacing 612 of the distal end segment 61.

The recess may comprise a slot traversing the thickness of the proximal wall 615 and extending from the outer surface of the distal end segment 61. In one example, the width of the slot is the width of the proximal wall 615 and the length of the slot is greater than the thickness of the circumferential wall plus the diameter of the steering wire, ensuring that a through-hole is formed of sufficiently large cross-section to allow the steering wire to pass therethrough in a longitudinal direction. The slot may be oriented with its length perpendicular to a plane on which the hinge members lie. In this manner both slots are oriented with their lengths traversing the plane on which the hinge members lie, best seen in FIG. 9b. The slots may be parallel to each other, as shown. The steering wire includes a first portion, a second portion, and an intermediate portion between the first portion and the section portion. Each of the segments comprises a first steering wire passage through-hole to accommodate the first portion of the steering wire and a second steering wire passage through-hole to accommodate the second portion of the steering wire. The steering wire may be secured at the distal end of the tip part by friction engagement with the proximal wall.

The first portion of the steering wire passes through the insertion guide into the inner spacing and out of the inner spacing through the first steering wire passage through-hole, and the second portion of the steering wire passes through the second insertion guide into the inner spacing and out of the inner spacing through the second steering wire passage through-hole, thereby placing the intermediate portion of the steering wire outside of the inner spacing. The intermediate portion is positioned adjacent the proximal surface of the proximal wall. In one example, the hinged member interferes with a straight path between the slots, therefore the steering wire is slightly bent inwardly due to the presence of the hinged member, increasing the friction which keeps the steering wire in place.

As shown, the first slot has a proximal surface cross-section, on the proximal surface of the proximal wall, equal to a distal surface cross-section, on the distal surface of the proximal wall.

The slots have a depth, extending from the outer surface inwardly, greater than a thickness of the outer wall plus a diameter of the steering wire.

Figure 9A:
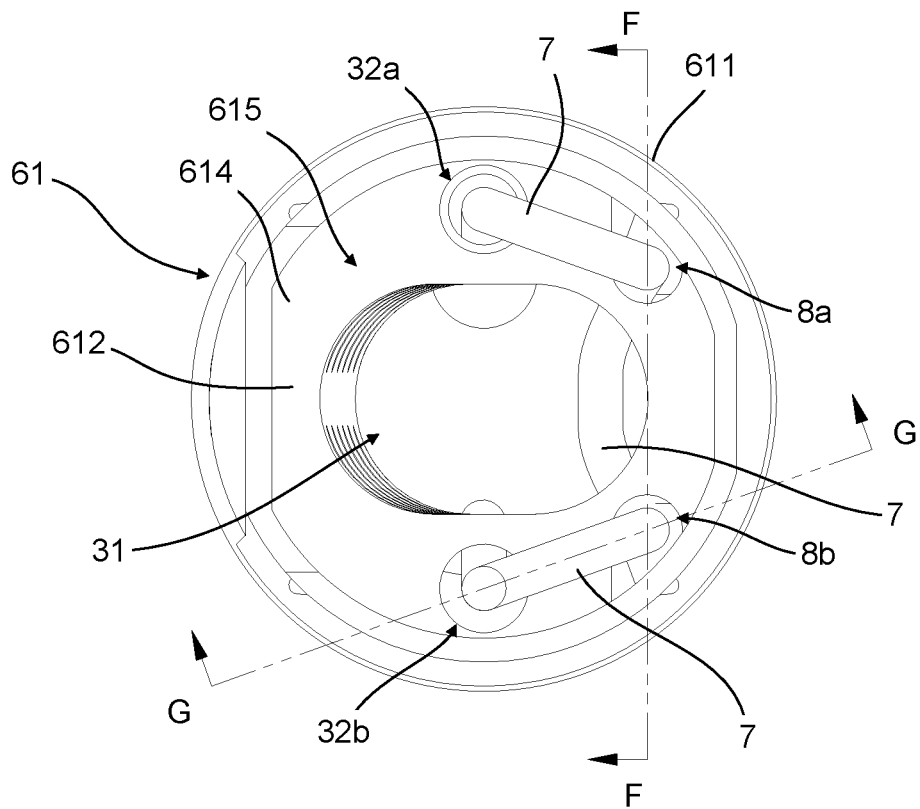
FIG. 9a shows a front or distal view of a second embodiment of the tip part
Figure 9B:
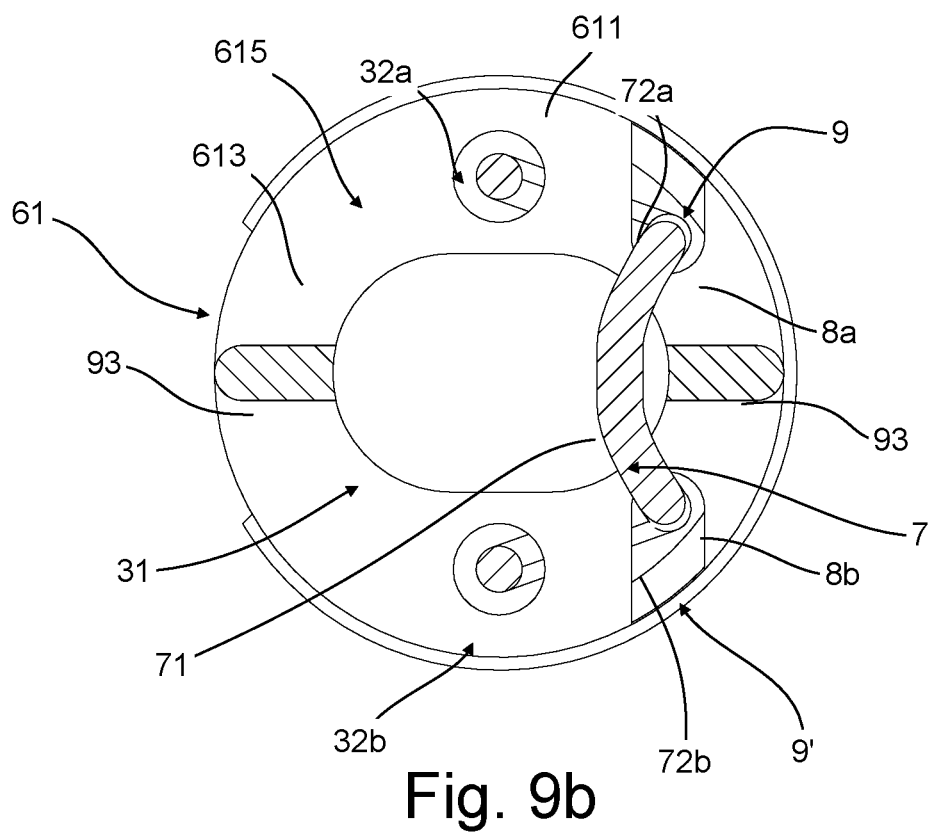
FIG. 9b shows a cross-sectional proximal view of the second embodiment of the tip part.
Figure 11A:
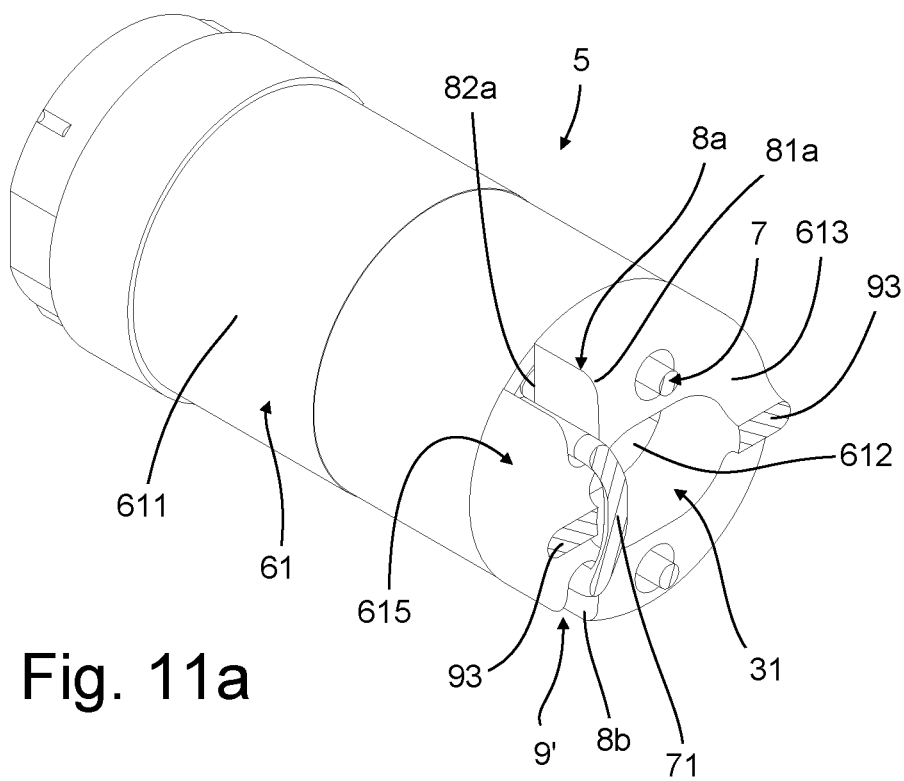
FIG. 11b shows a perspective view of the tip part shown in FIG. 11a, in which six intermediate segments of the tip part are included.
Figure 11B:
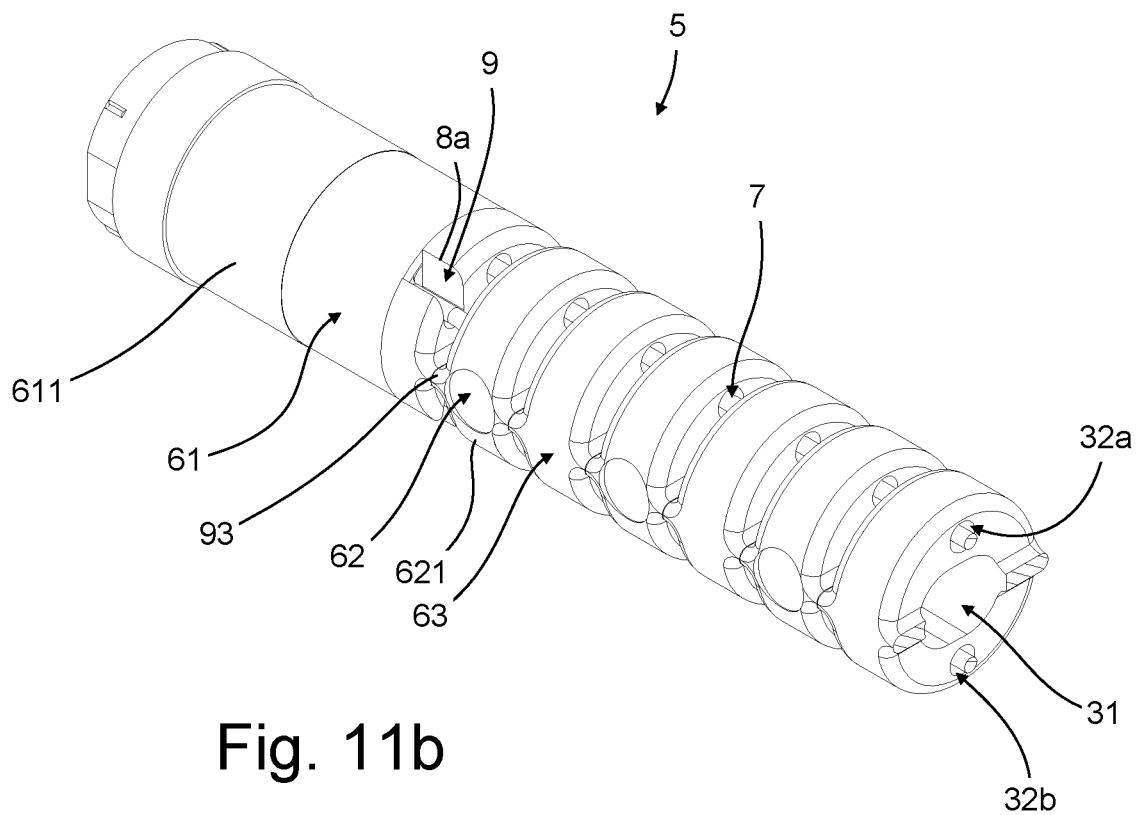

The method of securing a steering wire 7 in the tip part 5 according to the second embodiment is similar to the method of securing the steering wire 7 in tip part 5 according to the first embodiment, in that the first and second step are performed equally to in the first embodiment. In the third step of the method, the first end 7a of the steering wire 7 is inserted into the entry 81a of the distal portion 8a of the first insertion guide 9 and is slid along the bottom 83a of the distal portion 8a, and until the first steering wire end 7a enters the spacing 612 of the distal end segment 61 through the exit 82a of the distal portion 8a. In this way, the steering wire 7 is positioned more centrally compared to the outer circumferential surface 611 of the distal end segment 61, so that the outer circumference of the tip part 5 is unchanged and so that the steering wire 7 is positioned below the outer circumference of the tip part 5 after assembly of the steering wire 7 as can be seen in FIG. 9a.

The remaining steps of the method are performed in the same way as for the first embodiment. This method is then repeated by guiding the second end 7b of the steering wire 7 through the second insertion guide 9' in substantially the same way.

The following is a list of reference numerals used throughout this specification.

1 endoscope
2 handle
21 control lever
3 insertion tube
3a proximal end of insertion tube
3b distal end of insertion tube
31 cable passage
32a first steering wire passage
32b second steering wire passage
4 camera assembly
5 tip part
5a proximal end
5b distal end
6 main tube
61 distal end segment
611 outer circumferential wall
612 spacing
613 proximal surface
614 distal surface
615 proximal wall
second segment
621 outer circumferential surface
622 distal surface
623 proximal surface
63 third segment
64 proximal end segment
7 steering wire
7a first end of steering wire
7b second end of steering wire
71 intermediate steering wire bend
72a first steering wire bend
72b second steering wire bend
8a first distal portion
81a entry
82a exit
83a bottom
8b second distal portion
81b entry
82b exit
83b bottom
9 first insertion guide
9' second insertion guide
91 first proximal portion
91a entry
91b exit
91c bottom
92 second proximal portion
93 hinge member
PD proximal-distal axis

The invention claimed is:

1. An articulated tip part for an endoscope, the articulated tip part comprising:
a steering wire including a first portion, a second portion, and an intermediate portion between the first portion and the second portion; and
segments including a distal end segment and a second segment immediately proximal of the distal end segment, the distal end segment having an outer wall defining an inner spacing adapted to accommodate a camera assembly therein and a proximal wall connected to the outer wall, the proximal wall having a proximal surface, a distal surface, and a peripheral surface, the distal end segment having an outer surface including an outer surface of the outer wall and the peripheral surface of the proximal wall and enclosing the proximal wall, wherein the distal end segment and the second segment are interconnected by two hinge members to enable bending of the articulated tip part along a plane traversing the two hinge members,
wherein the distal end segment includes an insertion guide and a first steering wire passage through-hole, the insertion guide adapted to guide the steering wire and including an entry provided in the outer surface of the distal end segment, the insertion guide also including an exit in the distal surface of the proximal wall,
wherein the insertion guide comprises a slot in the proximal wall, the slot extending radially inwardly from the peripheral surface of the proximal wall and having a depth equal to or greater than a thickness of the outer wall and a diameter of the steering wire, and
wherein the first portion of the steering wire extends through the first steering wire passage through-hole and the insertion guide with the intermediate portion adjacent the proximal surface of the proximal wall and traversing the plane traversing the two hinge members.

2. The articulated tip part of claim 1, wherein the two hinge members are film hinges and/or integral hinges and/or living hinges.

3. The articulated tip part of claim 1, wherein the segments are integrally formed in one piece.

4. The articulated tip part of claim 1, wherein each of the segments has an outer surface, which includes the outer surface of the distal end segment, and wherein the outer surface of each segment is substantially cylindrically shaped, so that the articulated tip part has a uniform outer contour.

5. The articulated tip part of claim 1, wherein the intermediate section of the steering wire is secured at the tip part by friction engagement with the proximal wall of the distal end segment.

6. An endoscope comprising:
an articulated tip part according to claim 1; and
the camera assembly,
wherein the camera assembly is housed within the distal end segment of the articulated tip part, the articulated tip part being positioned at a distal end of the endoscope.

7. A system for visually inspecting a human body, the system comprising:
an endoscope according to claim 6 and a monitor, wherein the endoscope is connectable to the monitor, and the monitor is configured to present an image captured by the camera assembly of the endoscope.

8. The articulated tip part of claim 1, further comprising a second insertion guide including an entry provided in the outer surface of the distal end segment, wherein the first portion of the steering wire passes through the insertion guide into the inner spacing and out of the inner spacing through the first steering wire passage through-hole, and wherein the second portion of the steering wire passes through the second insertion guide into the inner spacing and out of the inner spacing through a second steering wire passage through-hole, thereby placing the intermediate portion of the steering wire outside of the inner spacing.

9. The articulated tip part of claim 8, wherein the second insertion guide comprises a second slot extending radially inwardly from the peripheral surface of the proximal wall and having a depth equal to or greater than the thickness of the outer wall and the diameter of the steering wire, and wherein the first slot and the second slot are parallel to each other.

10. The articulated tip part of claim 9, wherein the first slot and the second slot extend from the distal surface to the proximal surface.

11. The articulated tip part of claim 9, wherein the first slot has a proximal surface cross-section equal to a distal surface cross-section.

12. The articulated tip part of claim 9, wherein one of the two hinge members interferes with a straight path between the slot and the second slot.

13. The articulated tip part of claim 12, wherein the intermediate section is bent between the slot and the second slot toward a longitudinal axis of the articulated tip part.

14. A method for making an endoscope, the method comprising:
providing segments and a steering wire, the segments including a distal end segment and a second segment immediately proximal of the distal end segment, the distal end segment having an outer wall defining an inner spacing adapted to accommodate a camera assembly therein and a proximal wall connected to the outer wall, the proximal wall having a proximal surface, a distal surface, and a peripheral surface, the distal end segment having an outer surface including an outer surface of the outer wall and the peripheral surface of the proximal wall and enclosing the proximal wall, the distal end segment and the second segment being interconnected by two hinge members to enable bending of the articulated tip part along a plane traversing the two hinge members, the distal end segment including an insertion guide and a first steering wire passage through-hole, the insertion guide adapted to guide the steering wire and including an entry provided in the outer surface of the distal end segment, the insertion guide also including an exit in the distal surface of the proximal wall, the insertion guide comprising a slot in the proximal wall, the slot extending radially inwardly from the peripheral surface of the proximal wall and having a depth equal to or greater than a thickness of the outer wall and a diameter of the steering wire;
guiding a first end of the steering wire into the spacing of the distal end segment via the entry of the insertion guide;
guiding the first end of the steering wire out of the spacing via the first steering wire passage through-hole; and
guiding an intermediate portion of the steering wire through the plane traversing the two hinge members, the intermediate portion thus positioned adjacent the proximal surface of the proximal wall and traversing the plane traversing the two hinge members.

15. The method of claim 14, the method comprising:
guiding a second end of the steering wire into the spacing of the distal end segment via a second insertion guide; and
guiding the second end of the steering wire out of the spacing via a second steering wire passage through-hole.

16. The method of claim 15, wherein the second insertion guide comprises a second slot in the proximal wall, the second slot extending radially inwardly from the peripheral surface of the proximal wall and having a depth equal to or greater than the thickness of the outer wall and the diameter of the steering wire, and wherein the slot and the second slot are parallel to each other.

17. The method of claim 16, wherein one of the two hinge members interferes with a straight path between the slot and the second slot.

18. The method of claim 16, wherein the intermediate section is bent between the slot and the second slot toward a longitudinal axis of the articulated tip part.

* * * * *